(12) United States Patent
Demirbüker

(10) Patent No.: US 8,585,942 B2
(45) Date of Patent: *Nov. 19, 2013

(54) PROCESS AND ARRANGEMENT FOR PRODUCING PARTICLES UTILIZING SUBCRITICAL FLUIDS

(75) Inventor: Mustafa Demirbüker, Järfalla (SE)

(73) Assignee: XSpray Microparticles AB, Stockholm (SE)

( * ) Notice: Subject to any disclaimer, the term of this patent is extended or adjusted under 35 U.S.C. 154(b) by 440 days.

This patent is subject to a terminal disclaimer.

(21) Appl. No.: 12/745,055

(22) PCT Filed: Dec. 5, 2008

(86) PCT No.: PCT/SE2008/000683
§ 371 (c)(1),
(2), (4) Date: May 27, 2010

(87) PCT Pub. No.: WO2009/072953
PCT Pub. Date: Jun. 11, 2009

(65) Prior Publication Data
US 2010/0308483 A1    Dec. 9, 2010

Related U.S. Application Data

(60) Provisional application No. 61/019,391, filed on Jan. 7, 2008, provisional application No. 61/013,758, filed on Feb. 7, 2008.

(30) Foreign Application Priority Data

Dec. 7, 2007   (SE) ........................................ 0702735
Dec. 1, 2008   (WO) ................. PCT/SE2008/000674

(51) Int. Cl.
*B29B 9/00*   (2006.01)

(52) U.S. Cl.
USPC ................................... 264/5; 264/11; 264/14

(58) Field of Classification Search
USPC .................................................. 264/5, 11, 14
See application file for complete search history.

(56) References Cited

U.S. PATENT DOCUMENTS 5,118,528 A * 6/1992 Fessi et al. ............... 427/213.36
5,851,453 A   12/1998 Hanna et al.
(Continued)

FOREIGN PATENT DOCUMENTS

WO       99/30833       6/1999
WO       99/44733       9/1999
(Continued)

*Primary Examiner* — James Sanders
(74) *Attorney, Agent, or Firm* — Porter Wright Morris & Arthur LLP

(57) ABSTRACT

A method for producing particles of predetermined sized and/or morphology of a substance in a production arrangement comprising the steps of: i) mixing within a spray nozzle and under flow conditions a stream of a liquid solution in which the substance is dissolved with a stream of a fluid, and ii) passing the mixture in the form of a spray through a spray outlet of the nozzle into a particle collecting container, and iii) separating and collecting within the container the particles. The characteristic feature is that the solvent is a liquid and the fluid is an aqueous liquid in a subcritical state. Preferred nozzles have two coaxial internal transport conduits. One aspect is a production arrangement that can be used in the method. Its characteristic features are functions for a) recycling fluid used in the process, b) for including a make-up agent in the fluid stream, and/or increasing production by paralleling particle formation.

20 Claims, 5 Drawing Sheets

(56) References Cited

U.S. PATENT DOCUMENTS

| | | |
|---|---|---|
| 6,063,138 A | 5/2000 | Hanna et al. |
| 6,440,337 B1 | 8/2002 | Hanna et al. |
| 6,461,642 B1 | 10/2002 | Bisrat et al. |
| 6,475,524 B1 | 11/2002 | Bisrat et al. |
| 6,576,262 B1 | 6/2003 | Hanna et al. |
| 6,860,907 B1 | 3/2005 | Hanna et al. |
| 7,108,867 B2 | 9/2006 | Sundholm et al. |
| 7,150,766 B2 | 12/2006 | Hanna et al. |
| 7,985,058 B2 * | 7/2011 | Gray ................. 425/7 |
| 2004/0028646 A1 * | 2/2004 | Gross et al. ............. 424/78.38 |
| 2005/0206022 A1 * | 9/2005 | Pellikaan et al. ............ 264/11 |
| 2005/0214228 A1 * | 9/2005 | Begon et al. ............... 424/46 |
| 2006/0073087 A1 | 4/2006 | Hanna et al. |
| 2007/0009604 A1 | 1/2007 | Sundholm et al. |
| 2007/0116650 A1 | 5/2007 | Demirbüker |
| 2007/0231398 A1 * | 10/2007 | Van Lare et al. ............. 424/490 |
| 2008/0193518 A1 | 8/2008 | Zarkadas et al. |
| 2012/0090604 A1 * | 4/2012 | Foster et al. ............. 128/200.23 |

FOREIGN PATENT DOCUMENTS

| | | |
|---|---|---|
| WO | 01/15664 A2 | 3/2001 |
| WO | 02/058674 A2 | 8/2002 |
| WO | 02/068107 A2 | 9/2002 |
| WO | 03/008082 A1 | 1/2003 |
| WO | 2005/061090 A1 | 7/2005 |

* cited by examiner

PROCESS AND ARRANGEMENT FOR PRODUCING PARTICLES UTILIZING SUBCRITICAL FLUIDS

RELATED APPLICATIONS

The present application is a 371 of PCT/SE2008/000683 filed Dec. 5, 2008 and claims priority under 35 U.S.C. §119 to U.S. applications Ser. Nos. 61/019,391 filed Jan. 7, 2008 and 61/013,758 filed Feb. 7, 2008.

TECHNICAL FIELD

The invention relates to a method for controlled production of a batch of particles of predetermined sizes and/or morphology from a solution that comprises a particle-forming substance dissolved or dispersed in a solvent. The method comprises i) mixing the solution with a fluid within a spray nozzle, ii) forcing the mixture to leave the nozzle as a jet (spray) through a spray outlet of the nozzle, and iii) separating and collecting the formed particles from the mixture. Nucleation and particle formation are taking place subsequent to the mixing in the nozzle.

The invention also relates to a) a method for controlling size and morphology characteristics of the particles produced in the method in the preceding paragraph, b) an arrangement that can be used in the inventive methods, and c) a pharmaceutical formulation (composition) in which particles manufactured according to the method given in this specification have been incorporated.

The formed particles are typically intended to be used in compositions for in vivo use although other uses are also possible.

The terms "controlled" and "controlling" primarily refer to the repeatable production of batches in which the particles are within preset limits with respect to size characteristics, such as mean particle size, particle size distribution etc and inter-particle homogeneity regarding morphology (i.e. crystal characteristics of individual particles, e.g. degree of amorphousness and/or crystalline properties).

All patent applications and issued patents cited in the specification are in their entirety incorporated by reference.

TECHNICAL BACKGROUND

Various arrangements including nozzles that can be used in the particle forming technique given above are described in U.S. Pat. No. 5,851,453 (WO 9501221), U.S. Pat. No. 6,063,188 and US 2006073087 (WO 9600610), U.S. Pat. No. 6,440,337 (WO 9836825), WO 9944733, U.S. Pat. No. 6,576,262 (WO 9959710), U.S. Pat. No. 7,150,766 and U.S. Pat. No. 6,860,907 (WO 0103821), WO 0115664, US 2007116650 (WO 05061090) etc.

Se also our copending international patent application "Method and arrangement for the production of particles" PCT/SE2008/000674 filed Dec. 1, 2008.

Solution Enhanced Dispersion by Supercritical fluids (SEDS technique) is a particle formation technique of the kind defined above.

The use of supercritical fluids have resulted in promising results but primarily worked for laboratory scale production. When scaling up to pilot plant scale there have been increasing problems with obtaining sufficiently small particles (mean size) and/or particles having a sufficiently narrow size distribution.

The solvents for the particle-forming substance have been aqueous or non-aqueous depending on the solubility characteristics and kind of substance to be transformed to a particulate state. For aqueous solvents the problem with size and size distribution have been more pronounced than for non-aqueous solvents due to a stronger tendency for the primarily formed particles to aggregate. For biologically active substances, such as most proteins, which require a specific three-dimensional structure for activity, and other biopolymers, aqueous solvents are normally preferred since non-aqueous solvents and/or organic solvents often are denaturing.

A typical spray nozzle has contained separate internal conduits for the solution and the fluid. These conduits have merged in a mixing arrangement upstream of or at the spray outlet of the nozzle. In a typical variant one of the conduits is placed inside the other conduit at least when approaching the spray outlet and/or the mixing arrangement, e.g. with the outer conduit cylindrical and coaxial with the inner conduit and a merging angle between the two conduits and between the two streams of essentially 0°. The nozzle has typically been placed in a chamber (particle collecting chamber) in which the formed particles have been separated and collected from the solvent and fluid used. The productivity of particles has been low. Up-scaling has been difficult mainly due to the fact that particle size characteristics and/or morphology will change when increasing productivity by increasing nozzle parameters, such as flow velocities, internal conduit dimensions, concentration of particle-forming substance in the solution etc. The available intervals for mean sizes and size distributions of the particles have for many substances been unsatisfactory, in particular for particles that are intended for pharmaceutical uses. These problems have been most accentuated for batches in which the desired mean particle size is in the lowest part of the μm-range, e.g. ≤10 μm, such as ≤5 μm or ≤3 μm.

A promising solution to these problems is given by the spray nozzle presented in WO 2005061090. In this nozzle the stream of fluid is merging with the stream of the solution containing the substance at an angle β which is in the interval of 30°-150°. In the most important variants, the flow of one of the streams, e.g. the solution stream, at the point of merging is cylindrical with a direction coinciding with the direction of the axis of this cylindrical flow while the flow of the other stream is annular and directed radially outwards with a centre positioned on the axis of the cylindrical flow. See FIGS. 1-3 in WO 2005061090. It has been shown that the nozzle design presented in WO 2005061090 will facilitate increased productivity and improved control of morphology and particle mean size and size distribution. Thus it has been possible to lower mean sizes and prepare batches with narrower size distributions. In spite of the promising results obtained with this nozzle there is still a need for improvements facilitating still higher productivities and/or control of broader ranges of the size and morphology to cover a larger diversity of substances and their different uses.

Water-miscible organic solvents, such as ethanol, have been included as a modifier in the solution containing the particle-forming substance in order to facilitate extraction of water into the fluid thereby promoting nucleation and particle formation. See for instance U.S. Pat. No. 6,063,188 and US 2006073087 (WO 9600610). In other variants the fluid has been in a supercritical state and contained the modifier:

U.S. Pat. No. 7,108,867 and US 2007009604 (WO 2002058674) describe a process in which the particle-forming substance is dissolved in water together with an agent having a solubility with a negative temperature dependency, and the supercritical fluid contains a liquid that is miscible both with water and the supercritical fluid. The process is performed at a temperature above the cloud point of the agent.

U.S. Pat. No. 6,461,642 (WO 0030613) describes a process in which water is included in the supercritical fluid before mixing with the solution containing the particle-forming substance.

See also U.S. Pat. No. 5,851,453 (WO 9501221), U.S. Pat. No. 6,063,188 and US 2006073087 (WO 9600610).

Supercritical fluids containing a solvent have also been used for modifying preformed particles. See U.S. Pat. No. 6,475,524 (WO 0030614).

Recycling of the supercritical fluid and/or performing a SEDS process in an arrangement comprising several particle collecting chambers has been suggested in WO 9501221 and WO 9600610. The chambers are suggested to be run in sequence with harvesting one chamber while another chamber is started, i.e. a kind of continuous process.

A discussion of production of particles by anti-solvent precipitation from a solution containing the particle forming substance in dissolved form is given in US 20080193518 (Schering-Plough Corp.)

In spite of the good results with supercritical fluid, it has turned out that there are substances for which the particle-formation technique referred to above is insufficient with respect to obtaining batches with desired particle characteristics. Alternative economically feasible methods are desired that can be used for particle-forming substances that are not problematic when using methods that normally are considered feasible, taking into account costs related to a) fluid, b) the apparatus used for producing the particles, c) easiness of increasing productivity etc.

OBJECTS OF THE INVENTION

The primary objects are to provide improvements with respect to at least one of the above-mentioned problems, in particular solving problems related to productivity and/or control of size and/or morphology.

A first object thus is to design a new economically feasible method that is of the same kind as the method defined under the heading "Technical Field". The new method should preferably be applicable to one or more particle-forming substances preferably including at least one substance for which laboratory scale, pilot plant scale and/or large scale production of particles of predetermined and desired characteristics are problematic when using supercritical carbon dioxide as the fluid.

A second object is to controllably produce batches of particles, each of which batches has particles with a) a mean particle diameter in the interval $\leq 20$ μm, such as $\leq 10$ μm or $\leq 5$ μm or $\leq 3$ μm or $\leq 2$ μm, with a lower limit being 0.1 μm or 0.5 μm, and/or b) a particle size distribution with $\geq 80\%$ of the particles within an interval of a width of $\leq 30$ μm, such as $\leq 20$ μm or $\leq 15$ μm or $\leq 10$ μm or $\leq 5$ μm or $\leq 3$ μm or $\leq 2$ μm. Batches in which the width is even less, such as $\leq 1$ μm or $\leq 0.5$ μm, can be envisaged, preferably for batches with particle mean sizes of $\leq 3$ μm, and/or c) a particle size distribution in which at least 80% of the particles is within a size interval having the width of $\leq 75\%$, such as $\leq \pm 50\%$ or $\leq \pm 25\%$ of the mean particle diameter.

The terms "particle size", "particle size diameter" and "particle size distribution" in this specification refer to values obtained as given in the Experimental Part (laser diffraction by the use of Mastersizer 2000 from Malvern Instruments Ltd, Worcestershire, United Kindom). For the meaning of "mean particle size" or "mean particle diameter" see also the Experimental Part.

A third object is to enable controlled production of batches of particles, each of which batch has particles with improved inter-particle homogeneity with respect to morphology features, such as crystal type or degree of amorphousness and/or crystalline characteristics. In other words this subobject typically means production of batches in which $\geq 50\%$, such as $\geq 60\%$ or $\geq 70\%$ or $>80\%$ or $\geq 90\%$ or $\geq 95\%$, of the individual particles of a batch have the same balance between amorphousness and crystalline features and/or between different crystal forms.

A fourth object is to render it possible to controllably produce batches of particles with a productivity of $\geq 0.5$ g/h, such as $\geq 1.0$ g/h or $\geq 2.0$ g/h or $\geq 5.0$ g/h or $\geq 10$ g/h per chamber used for separating and collecting the particles produced or per production arrangement in which there are one or more particle collecting chambers. This subobject includes providing a production arrangement in which these intervals are feasible.

A fifth object is to accomplish a combination of two or more of the objects and/or subobjects given above. Preferred combinations include productivity levels as given above.

FIGURES

Figure 4A:
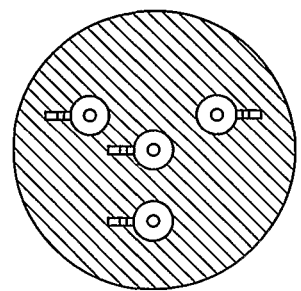
Figure 4B:
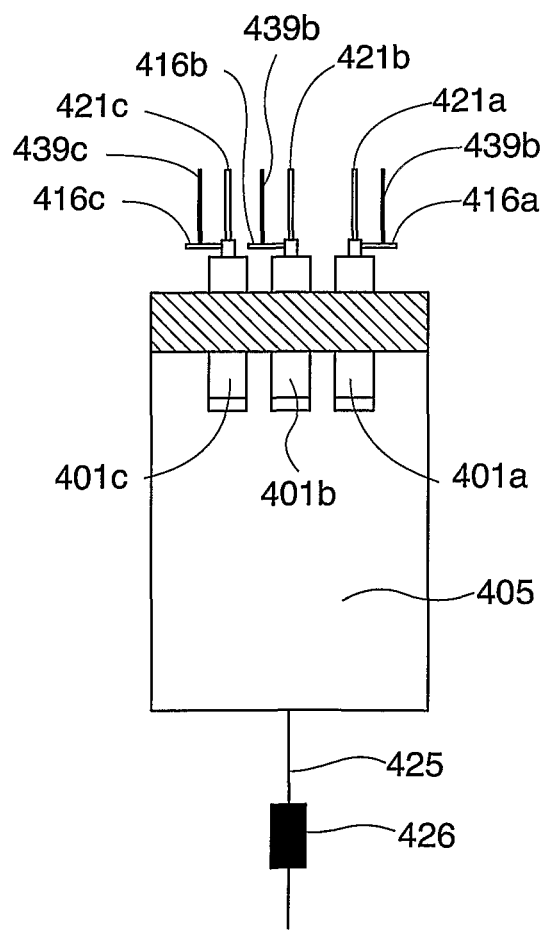

FIGS. 4a-b illustrate a collecting chamber containing two or more spray nozzles. FIG. 4a shows the collecting chamber from above while FIG. 4b gives a side view.

Figure 5A:
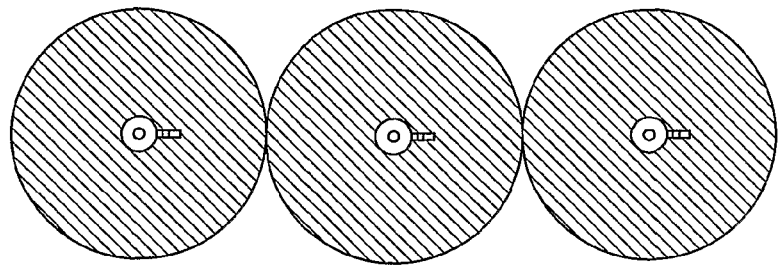
Figure 5B:
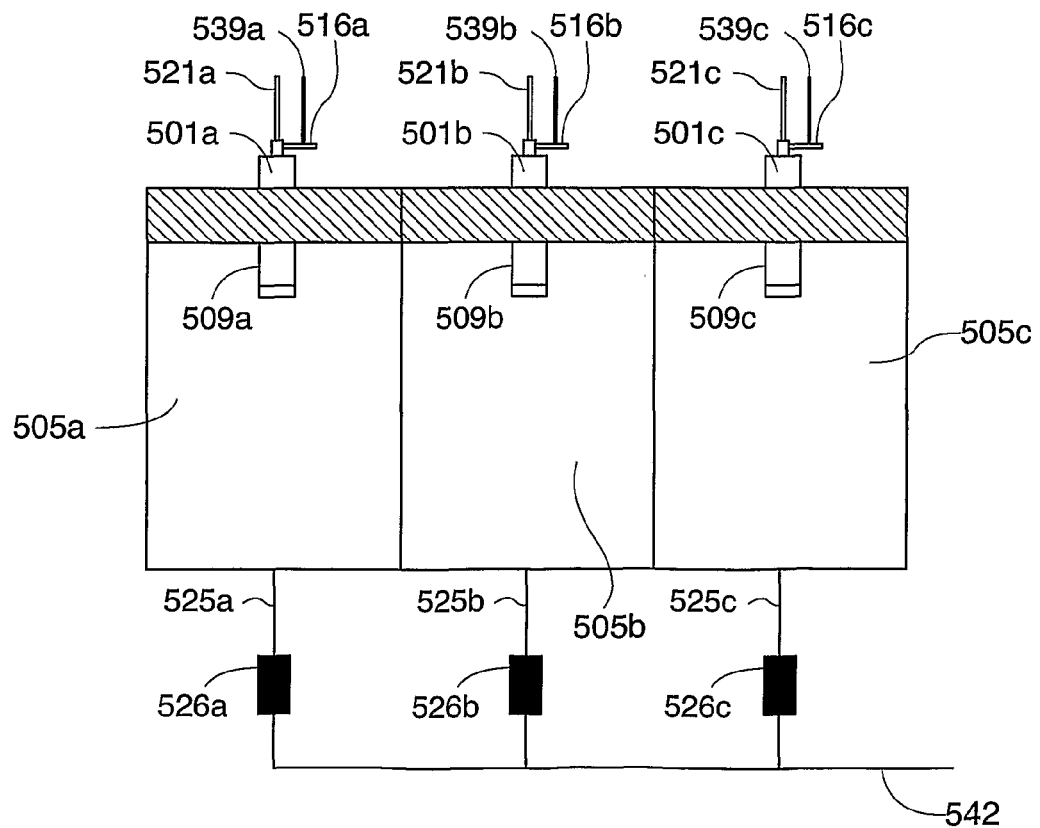

FIGS. 5a-b illustrate the presence of two or more particle collecting chambers in the same production arrangement. FIG. 5a shows the collecting chambers from above while FIG. 5b gives a side view of them.

Figure 6A:
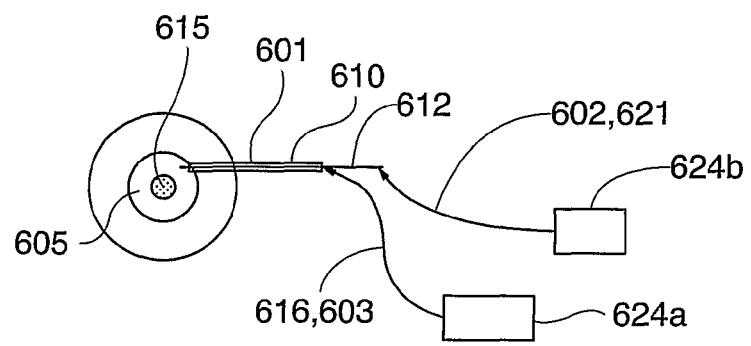
Figure 6B:
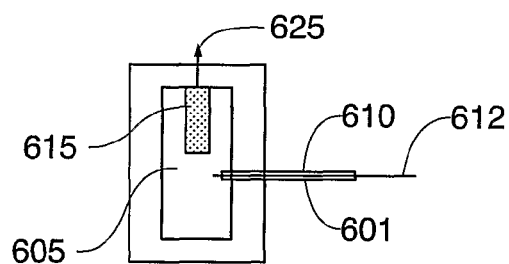

FIG. 6a-b illustrates an arrangement with a nozzle based on two coaxial internal transport conduits (one for the fluid and one for the solution) and a merging angle of about V.

Figure 2:
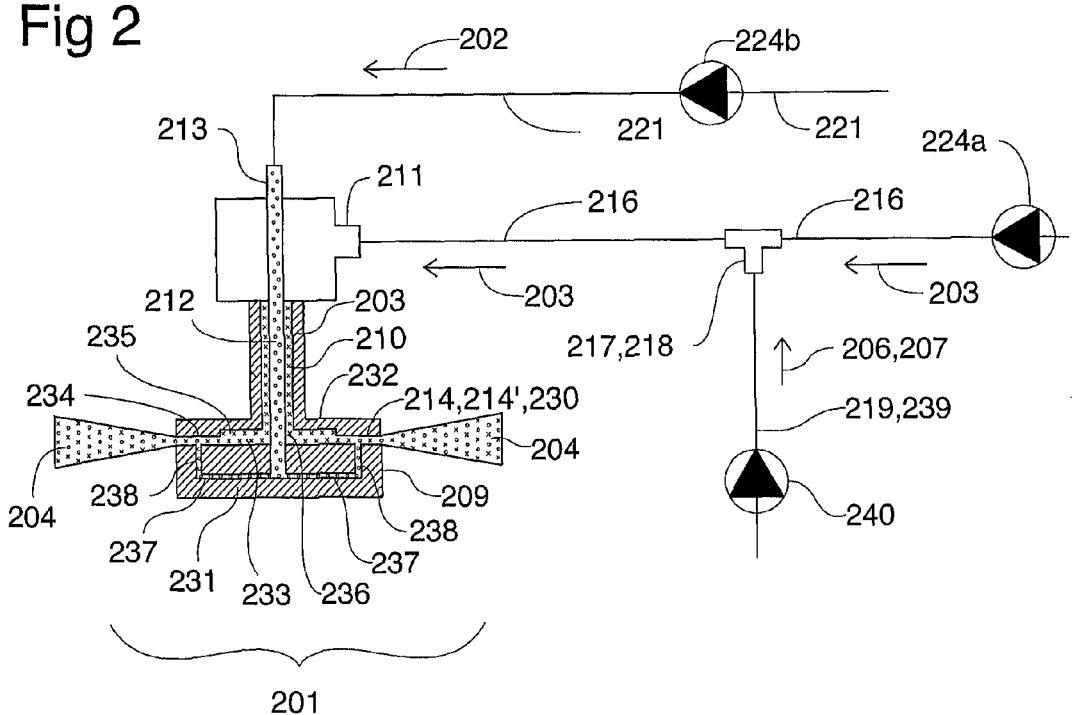
FIG. 2 illustrates a preferred nozzle and corresponds to FIGS. 1-3 of WO 2005061090.
Figure 7:
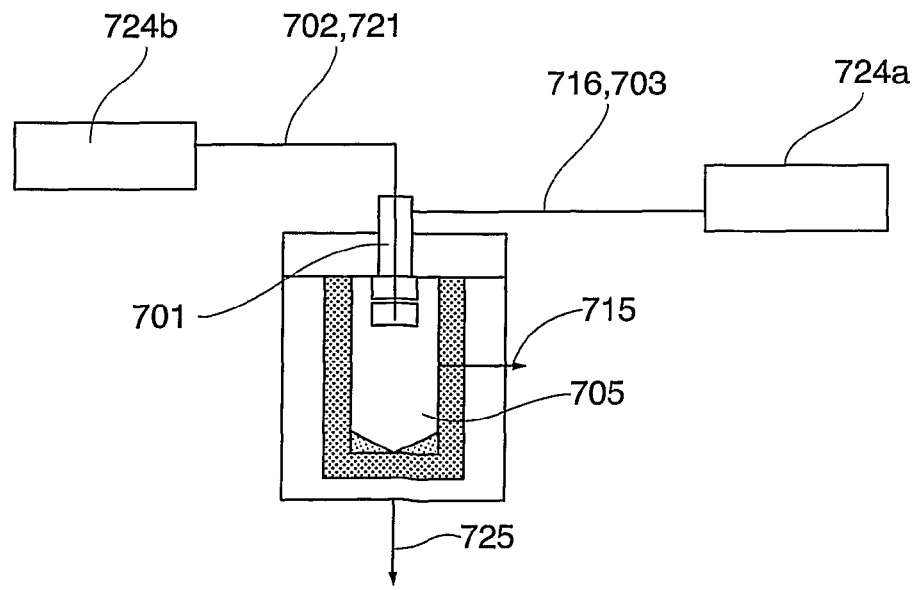

FIG. 7 illustrates another arrangement with the nozzle described in FIG. 2. Two coaxial internal transport conduits (one for the fluid and one for the solution) and a merging angle of about 0°.

Reference numerals in the figures comprise three digits. The first digit refers to the number of the figure and the second and third digits to the specific item. Corresponding items in different figures have as a rule the same second and third digits.

THE INVENTION

The present inventor has recognized that these objects at least partially can be accomplished if water in a subcritical state is used as the fluid in the method defined on page 1, $1^{st}$ paragraph. It has further been found that it is favourable for the method and the arrangement if the nozzle has two internal transport conduits which are coaxial to each other as discussed below in this specification. One of these conduits is for the fluid and the other one for the solution.

The present inventor has also recognized that partial accomplishment can also be gained if the fluid entering into the mixing (step (i)) is allowed to contain an agent influencing the sizes of the particles obtained, i.e. a so-called "make-up agent", preferably without causing separation of the fluid or of the solution-fluid mixture into distinct phases (a liquid and a fluid phase, for instance). The make-up-agent can be introduced into the fluid stream, i.e. upstream of the position of the mixing of the fluid stream with the liquid stream. Typical positions for introduction are a) a storage tank for the fluid located upstream of the spray nozzle, or b) a transport conduit between such a storage tank and the nozzle including to various functions that may be part of or connected to (=located along) the conduit, or c) to a transport conduit for the fluid within the nozzle, i.e. between the inlet of this conduit and the position of mixing in step (i). The effects of adding a make-up agent not causing liquid/fluid phase separations at these positions on particle sizes and/or morphology are tremendous and unexpected.

The present inventor has also recognized that it is not possible to reach a sufficient up-scaling of the productivity for a profitable large scale production of particles by a) increasing dimensions of nozzles or parameters such as flow rate, concentrations etc, or b) running several nozzles/chambers in sequence. In stead it is more feasible to parallel the spraying step in the arrangement by running several spray nozzles at least partially in parallel. In other words by using a production arrangement in which there are (i) two or more spray nozzles placed in the same collecting chamber and/or (ii) two or more collecting chambers containing one, two or more spray nozzles.

A main aspect of the invention is a method for producing a batch of particles of a substance in which the particles have predetermined sizes (primarily measured as mean particle diameter and/or particle size distribution) and/or morphology. The method comprises the steps of:

(i) mixing within a spray nozzle (101,201,301) and under flow conditions a stream of a solution (102,202) in which the particle-forming substance is dissolved or dispersed in a solvent with a stream of a fluid (103,203) that is capable of acting as an anti-solvent,
(ii) passing the mixture obtained in step (i) in the form of a spray (204) through a spray outlet (109,209,309) of the nozzle (101,201,301), and
(iii) separating and collecting the particles from said mixture.

The ratio between the volumetric flow velocities in the solution stream (102,202) and the fluid stream (103,203) and/or the concentration of the particle-forming substance in the solution are selected to promote nucleation and formation of the particles in the mixture. The nozzle (101,201,301,401, 501) is in spray communication with a particle collecting chamber (105,405,505) in which step (iii) is carried out. Spray communication in this context means that the spray is directed into the collecting chamber.

The main characteristic feature of the method comprises that the solvent is a liquid and the fluid is in a subcritical state in the form of an aqueous liquid. With preference the nozzle comprises at least two internal transport conduits that are coaxial to each other and intended for nozzle internal transportation of fluid and solution, respectively. Further details about the solvent and the fluid and the coaxial conduits are given below under the headings "The fluid stream and the solution stream" and "Spray nozzle".

The method of the invention may in subaspects also comprise:

A) the additional step (iv) of providing one or more make-up agents (107,207) to the fluid stream (103,203), i.e. at a position which is upstream of the mixing position, and/or
B) performing at least steps (i) and (ii) simultaneously in two or more separate spray nozzles (401$a,b$ . . . , 501$a,b$ . . . ) that belongs to the same production arrangement in which there are one, two or more particle collecting chambers in spray communication with the spray nozzles with
 (a) at least two of the nozzles placed in spray communication with the same particle collecting chamber (405), and/or
 (b) each of two or more of the particle collecting chambers (505$a,b$ . . . ) containing at least one nozzle (501$a,b$ . . . ) (containing=placed in spray communication with).

The method is typically performed in the production arrangement described below. In the case of several spray nozzles and particle collecting chambers they are part of the same production arrangement. The meaning of the term "simultaneous" is given below.

The mean size, the size distribution and morphology of particles in the batches produced are typically within the limits given under the heading "Objects of the invention".

Steps (i)-(iii), possibly with one or more additional steps inserted between steps (i) and (ii), and/or between steps (ii) and (iii).

The pressure drop across the nozzle (101,201,301), the kind of solvent in the solution, the kind of fluid, the ratio between the volumetric flow velocities of the solution and the fluid streams at mixing, the concentration(s) and kind of the make-up agent(s) in the fluid at the mixing etc are selected to be effective in promoting nucleation and particle formation giving particles of the predetermined sizes and/or morphology at the spray outlet (109,209,309). Preferably neither mixing of the fluid stream with the solution stream nor the make-up agent with the fluid stream should cause phase separation into liquid/fluid phases, i.e. a one-phase system is preferred (except for the desired particles formed in the process).

Another main aspect of the invention is a production arrangement (100) (=apparatus, production equipment, production apparatus) to be used in the method defined on page 1, 1$^{st}$ paragraph. The arrangement is illustrated in the drawings and comprises at least:

a) a spray nozzle (101,201,301) having an internal transport conduit (210 or 212,310 or 312) with an inlet (111,113, 211,213) for the fluid, an internal transport conduit (210 or 212,310 or 312) with an inlet (111,113,211,213) for the solution, and a mixing arrangement (114,214,314) for mixing the fluid and the solution with each other downstream of the internal transport conduits (210,212,310,312), and a spray outlet (109,209,309),
b) a chamber (105) containing the spray outlet (109) and a separating function (115) for separating and collecting the produced particles from the solution-fluid mixture (=particle collecting chamber), and
c) a transport conduit (116,216) external to the nozzle for transferring fluid (103,203) to the fluid inlet (111,113,211, 213) of the nozzle (101,201).

The term "containing" in (b) means that the spray is directed into the particle collecting chamber (105), i.e. is in spray communication with the chamber.

The main characteristic feature of the arrangement is that it comprises a) one or more inlet conduits for introducing a make-up agent (107,207) and/or fluid previously used (106,206) in the process (method) at a position in the fluid stream (103,203) upstream of the mixing arrangement (114,214), e.g. via inlet/conduits (117/139,217/239 and 118/119,218/219, respectively) into the fluid stream (103,203) of the process, i.e., and/or
b) two or more spray nozzles (401$a,b$ . . . , 501$a,b$ . . . ) with at least two of them being placed in spray communication with
 i) the same collecting chamber (405) and/or
 ii) different collecting chambers (505$a,b$ . . . ) each of which chambers containing at least one, two or more spray nozzles, and/or
c) a recycling function (118+119+120,218+219) for recycling fluid (106,206) used in the process into the fluid stream (103,203) via at least one inlets (118,218), i.e. at a position upstream of the mixing arrangement (114,214).

The recycling function is primarily intended for variants of the methods defined on page 1, 1$^{st}$ paragraph, for which the fluid is a non-aqueous supercritical or subcritical organic or inorganic fluid. See for instance discussion about fluids below.

As illustrated in the drawings, the arrangement (100) also comprises a transport conduit (121,221) for transferring the solution to the nozzle (101,201) in addition to the fluid transport conduit (116,216) already mentioned. One or both of these nozzle external transport conduits can in their upstream end be connected to a storage tank for the fluid or the solution (122 and 123, respectively) They are typically also equipped with the appropriate functions for control of temperature (including e.g. heating elements (141) and/or pressure and flow control (124a,b,c) (including e.g. valves, pumps etc) for supporting the temperature, flow velocities and/or pressures required in the collecting chamber (105) and in the fluid stream (103,203) upstream of this chamber (105), e.g. supporting a sub- or supercritical state of the fluid and/or the solution/fluid-mixture and/or the predetermined mean size, size distribution and/or morphology of the particles to be produced. A storage tank, e.g. for the fluid (122), can be in the form of a pressurized tube or may be connectable to such a tube if a supercritical fluid is used.

If the recycling function (c) is present there preferably is a function (120) for separating fluid from the solution/fluid-mixture, i.e. to give fluid depleted in solvent. This function (120) is placed downstream of the particle collecting chamber (105). If present this function (120) typically is in the form of a cyclone. The downstream end (outlet) of the collecting chamber (105) and the upstream end of the fluid separating function (120) are connected to each other via a transport conduit (125) typically containing a back pressure regulator (126) for enabling changes in flow velocity through the spray outlet (109). The fluid separating function (120) typically contains an outlet conduit (127) with a valve (128) for enabling outlet of solvent freed from (e.g. depleted in) fluid and an outlet (129) for fluid freed from (e.g. depleted in) solvent. At this position the solvent is in the liquid state and the fluid in the gas state if used in a supercritical state in the nozzle. In variants adapted for recirculation of fluid back into the process, the fluid outlet conduit (119,219) of the fluid separating function (120) is typically connected via an inlet conduit (118,218) to the fluid stream (103,203), i.e. at a position upstream of the mixing arrangement (114,214) as discussed elsewhere in this specification.

The Spray Nozzle

As already mentioned the spray nozzle comprises an outlet (109,209,309) in which a spray (jet) can be formed, an arrangement for mixing (214,314) the solution with the fluid, and internal transport conduits (210,212,310,312) for the fluid and the solution, respectively. In preferred variants the nozzle also comprises a mixing microcavity (214') as part of the mixing arrangement (214) and/or an outlet transport conduit (230) guiding the mixture from the mixing arrangement (214) to the spray outlet (109). If both an outlet conduit (230) and a mixing cavity (214') are present they can partially or fully coincide. In preferred variants one of the above-mentioned transport conduits (210,212,310,312) are inside the other, preferably by being coaxial with each other, as described above for earlier known spray nozzles used in the field.

The mixing in the mixing arrangement (214,314) is promoted by creating turbulence when the fluid stream and the solution stream merge. For this purpose the mixing arrangement may contain some kind of hinder for forward flow at or downstream of the position where the solution stream and the fluid stream merge, for instance by designing the conduits concerned (e.g. as a mixing cavity) with mechanical flow disturbance means, such as with an abrupt turn or corner (typically ≥30°) and/or an abrupt change in cross-sectional dimension (widening or narrowing). Suitable mixing arrangements comprise that the solution stream (202) and the fluid stream (203) merge at an angle β selected in the interval of 0°-180°, typically with a mixing cavity downstream of the point of merging. Preferred merging angles β are selected in the interval 30°-150°, such as 85°-105° with 90° being the most preferred value. In most cases this also means that the nozzle internal transport conduits (210,212,310,312) for the solution and the fluid, respectively, are merging at an angle β' that also is selected in the same interval as the angle β with the same preferences.

Figure 3:
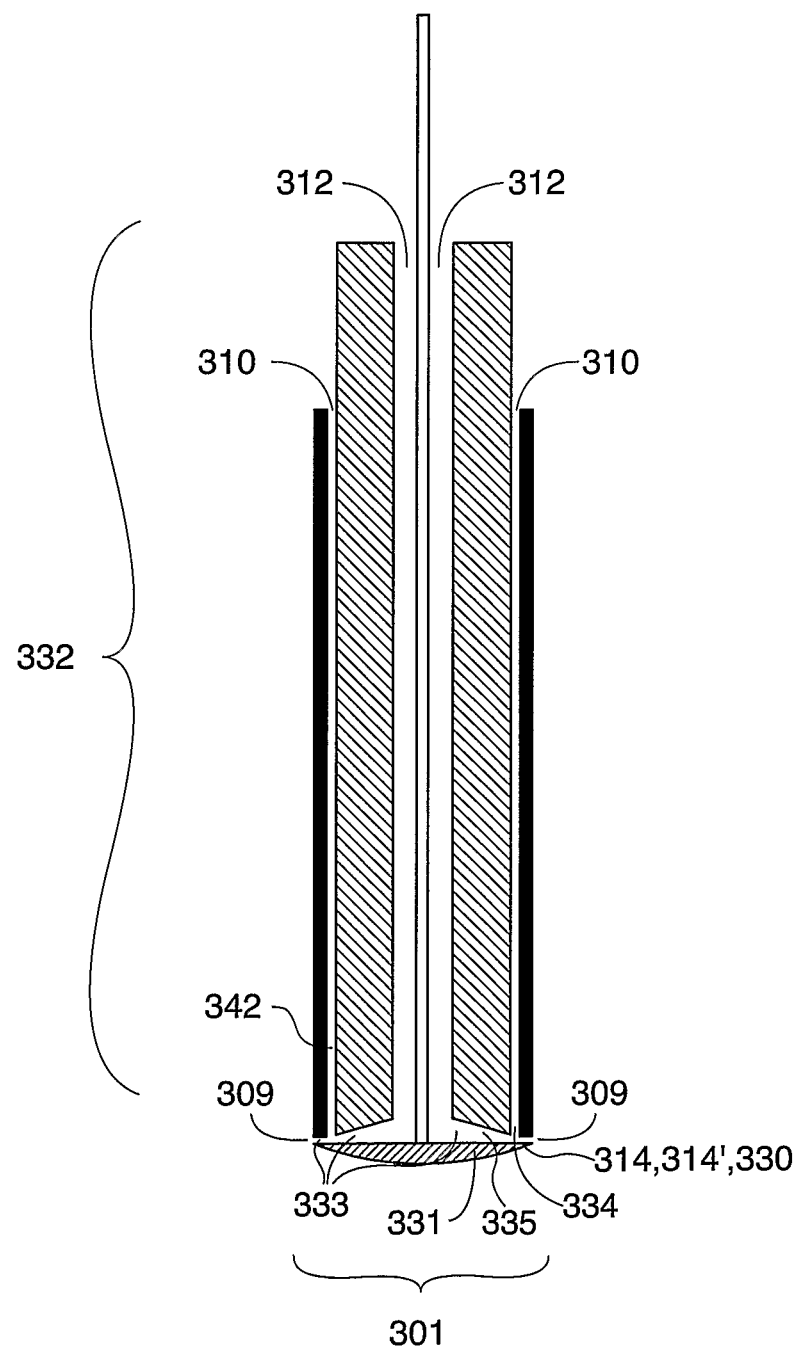
FIG. 3 illustrates another preferred nozzle and corresponds to FIG. 5 of WO 2005061090.

Preferred nozzle internal transport conduits are coaxial and are illustrated in FIGS. 2 and 3 with absolute preference for the type described in FIG. 2. These nozzles have a downstream part (231,331) and an upstream part (232,332). The downstream part hinders forward flow through the downstream end of at least one of the nozzle internal transport conduits (210,212,310,312) thereby transforming the flow direction of the stream passing through this end into a disc-shaped annular flow comprising a radial component directed outwards and passing through a slot (233,333) defined between the downstream part (231,331) and the upstream part (232,332). This disc-shaped flow then merges with the flow of the other internal transport conduit at a merging angle β that is in the interval given above with the same preferences. The merged flow leaves the nozzle as an annular spray which preferably is directed radially outwards, possibly comprising an axial component. If no axial component is at hand the spray direction will define an angle of 90° with the axial direction of the coaxial internal transport conduits (=Of the nozzle). If an axial component is present the angle will deviate from 90°. Each internal transport conduits (210,212) ends when merging with the other one of them (at the mixing arrangement), i.e. a nozzle internal transport conduit for which the flow has been hindered by the downstream part (231,331) comprises also a part (234+235,334+335) of the slot (233,333).

The variant of FIG. 2 thus comprises a downstream part (231) and an upstream part (232) (=lower and upper parts in the drawing). In the upstream part (232) there is an inner transport conduit (212) and an outer cylindrical transport conduit (210) coaxial with the inner transport conduit (212). The slot (233) defined between the downstream and the upstream parts (231,232) encompasses in the downstream direction an annular disc-shaped conduit (234+235) plus an annular mixing arrangement/mixing cavity (214/214') plus an annular outlet conduit (230) for the mixture obtained plus an annular spray outlet (209). Forward flow in the outer cylindrical transport conduit (210) is hindered by the downstream part (231) and transformed to a disc-shaped annular flow directed radially outwards in the disc-shaped conduit (234, 235). The downstream part (231) is also designed to hinder forward flow of the stream in an inner transport conduit (212) but the hindering is taking place within the downstream part (231) by transforming the inner stream to a cylindrical stream of opposite flow direction with a diameter which is larger than the diameter of the cylindrical flow the original outer stream. This latter flow transformation is accomplished by designing the downstream part (231) with a forward extension (236) of the inner transport conduit (212) followed by a disc-shaped conduit (237) and a thereto connected cylindrical conduit (238) going in a direction that is opposite to the direction of the forward extension (236) so that it can merge with part (234) of the disc-shaped conduit (234+235) downstream of the outer transport conduit (210) at the upstream end of the mixing arrangement (214). The merging angle β' is 90° in this FIG. 2. Other merging angles can be accomplished by a) designing the surface of the downstream part (231) at the point of the merging with an angle < or >90° relative to the axis of the cylindrical conduit (238), or b) making the cylindrical conduit (238) conical.

If merging angles different from 90° are created in this manner it is then appropriate to also design the mating surface of the upstream part with a matching curvature.

FIG. 3 gives a variant with a downstream hindering part (331) which contains no parts of the internal fluid and solution transport conduits. The upstream part (332) comprises the coaxial cylindrical transport conduits (310,312), one for the solution and one for the fluid. The downstream part (331) hinders forward flow in both of the conduits at the same position. The slot (333) between the two parts provides for transformation of a cylindrical stream to a disc-shaped stream with a flow directed radially outwards in the disc-shaped conduit (334+335), mixing with the outer cylindrical stream in the annular mixing arrangement (314) and transportation of the mixture in the annular outlet transport conduit (330) to an annular spray outlet (309). The merging angles β and β' are 90°. Other merging angles can be accomplished by making the surface of the downstream part at the point of merging conical and design the mating surface of the upstream part with a matching curvature.

For nozzle variants in which the internal transport conduits (210,212,310,312) are coaxial it is preferred to use an inner transport conduit (212,312) for the solution stream (202) and an outer transport conduit (210,310) for the fluid stream (203) as indicated in the drawings.

In still other variants of spray nozzles which contain inner and outer internal transport conduits there is no downstream part hindering forward flow of the streams. These kinds of nozzles are believed to be less preferred and are illustrated in FIGS. 3 and 4 of U.S. Pat. No. 5,851,453 (WO 9501221). The mixing arrangement of the nozzles illustrated in these figures starts at the outlet of the inner conduit (31) and extends to the outlet of the outer conduit (41) that also is the outlet of the spray nozzle. The mixing cavity is defined between the outlets of the inner and outer conduits. The merging angle between the transport conduits for solution and fluid, respectively, will be approximately 0°. Reference numerals are the same as given in WO 9501221 (U.S. Pat. No. 5,851,453). See also WO 9600610 (U.S. Pat. No. 6,063,188 and US 2006073087).

In other variants of nozzles, the solution/fluid mixture is mixed with other streams, e.g. containing a sub- or supercritical fluid or a liquid/solvent, before exiting through the spray outlet/into the particle collecting chamber. See for instance U.S. Pat. No. 6,440,337 (WO 9836825).

The spray direction of the above-mentioned spray nozzles in which one of the transport conduits is placed inside the other may be purely axial and/or purely radial in relation to these transport conduits.

The adjustment of the flow velocity through the nozzle is done by adjusting the pressure difference across the nozzle (201,301), e.g. by adjusting the back pressure regulator (126) downstream of the particle collecting chamber (105) and/or changing the output from the pressure regulation means (pumps, valves etc) (124*a,b*) upstream of the nozzle. In variants having adjustable flow hinders these can be used for fine tuning of the flow velocity through the spray outlet (209,309). For instance in the kind of nozzles which is illustrated in FIGS. 2 and 3 and also in US 2007116650 (WO 05061090), the width of the slot (233,333) formed between the downstream part (231,331) and the upstream part (232,332) is typically adjustable by arranging so that either one or both of the two parts are axially movable relative to each other. By changing the width of the slot the volumetric flow velocity through the slot (233,333) will change. Fine tuning of the flow velocity through the width is obtained if the two parts (231, 232,331,332) are pressed towards each other by a string, gas cushion or other resilient and/or compressible means which are linked to an adjustable compressing force. See further US 2007116650 (WO 05061090).

Suitable dimensions of conduits and openings in the nozzles given above can be found in the patents and patent applications cited above.

During the method defined on page 1, $1^{st}$ paragraph, utilizing subcritical fluids that at atmospheric pressure and room temperature are liquids, the pressure within the arrangement immediately upstream and downstream of the nozzle is typically significantly lower than when supercritical fluids are used, but typically >1 bar, such as ≥1.25 bar or ≥2 bar or ≥5 bar, with typical upper limits being 30 bar or 20 bar or 10 bar. The temperature can be down to room temperature or even lower provided the fluid remains in a liquid state. In this category falls the method of the invention, i.e., the fluid is an aqueous liquid.

For variants of the method defined on page 1, $1^{st}$ paragraph, utilizing supercritical fluids, the pressure inside the arrangement immediately upstream and downstream of the nozzle is typically above the critical pressure Pc and critical temperature Tc of the fluid used. For the pressure this typically means a pressure in the interval (1.0-7.0)×Pc or in the interval ≥10 bar, suitably ≥20 bar with preference for ≥30 bar, higher than Pc with illustrative upper limits being 100 bar, 200 bar and 300 bar higher than Pc. The expression "above Tc" (in ° C.) typically means within (1.0-4.0)×Tc or within the interval of ≥5° C., suitably ≥10° C. with preference for ≥15° C. above Tc with illustrative upper limits being 10° C., 40° C. and 50° C. above Tc.

For fluids that are in a gaseous state at room temperature and atmospheric pressure and used in a subcritical state the pressure is typical within the intervals given above and the temperature below the critical temperature, such as in the interval (0.9-1.0)×Tc For methods as defined on page 1, $1^{st}$ paragraph, utilizing subcritical fluids, suitable pressure drops across the nozzle (201,301) is typically found in the interval ≥1.25 bar or ≥2 bar or ≥5 bar, with typical upper limits being 30 bar or 20 bar 10 bar, with preferred values being in the interval 1.5-10 bar such as 2-5 bar. For methods utilizing supercritical fluids, suitable pressure drops can be found in the interval of 10-60 bar, such as ≥10 bar but ≤50 bar, such as ≤40 bar or ≤30 bar.

The flow velocity through the spray outlet (209,309) should be selected in the interval of 50-200 ml/min with preferred values in many cases being at least 75 ml/min. At the upstream end of the mixing arrangement (114,214,314) the volumetric flow velocity of the solution stream (102,202) containing the particle-forming substance is typically selected to be less than, such as ≤90% or ≤80% or ≤70%, of the flow velocity that give saturation of the solvent of the solution in the supercritical fluid at the prevailing pressure and temperature, i.e. solvent/fluid phase separations should be avoided. In typical variants suitable volumetric flow velocities of the solution stream (102,202) at the upstream end of the mixing arrangement (114,214,314) can be found in the interval of 0.01-20%, such as ≥0.1% or ≥0.5% or ≥1% and/or ≤15%≤ or ≤10% or ≤5%, of the of the flow velocity of the fluid stream (103,203). If a make-up agent is used the volumetric flow velocity of the stream of the make-up agent (107,207) at its mixing with the fluid stream at inlet conduit (117,217) is typically selected in the same relative percentage interval as the flow velocity of the solution containing the particle-forming substance, typically without causing phase separations when the streams are mixed. If the make-up agent is present in recycled fluid (106,206), suitable flow velocities of the make-up agent as such relative to the velocity of the fluid stream at inlet conduit (118,218) can be found in the lower part of the 0.01-20% interval e.g. ≤5% or ≤3% or ≤1% depending on how effective the fluid separating function (120) is or if further make-up agent, vehicles etc have been added downstream of the separating function (120).

The Particle Collecting Chamber

In the inventive arrangement there is at least one particle collecting chamber (105,405,505). A particle collecting chamber may contain at least one spray nozzle (101, 401a,b..., 501a,b...).

Figure 1:
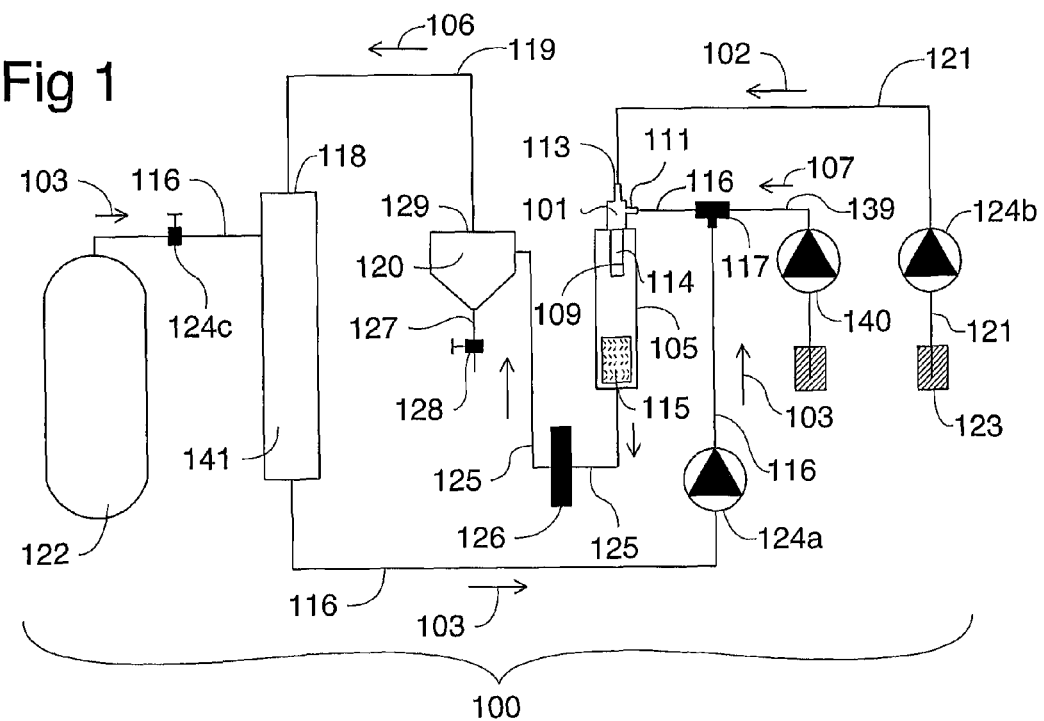
FIG. 1 illustrates a typical one-nozzle variant of the inventive arrangement

In FIG. 1 is illustrated a variant of the particle collecting chamber to which is associated one nozzle. This variant is discussed above. See also below.

In FIGS. 4a-b there is shown a collecting chamber (405) carrying two or more nozzles (401a,b...) with spray outlets. The transport conduits for the fluid (416a,b, ...), for the solution (421a,b) and for the make-up agent (439a,b...) are in the upstream direction connected to a storage tank for fluid, solution and make-up agent, respectively. On the downstream side of the chamber there is an outlet conduit (425) with a back-pressure regulator (426). The outlet conduit (425) may downstream of the back-pressure regulator transport the solvent/fluid mixture to waste or to a separating function in which the fluid is separated from the solvent and possibly recycled back into the fluid stream.

The spray outlets of the nozzles (401a,b...) in the same chamber (405) are typically placed at the same level, symmetrically around a central axis of the chamber, and in an upper part of the chamber with the axis of the cylindrical conduits and/or the coaxial conduits typically being directed vertically with preferably a downward flow direction. The number of nozzles in a chamber is typically one, two, three, four, five or more with a typically upper limit of 10 or 20. The maximum number of optimally placed nozzles in a chamber is determined by the chamber diameter perpendicular to the central axis of the chamber. For a chamber having a cross-sectional diameter of 20 cm the optimal maximum number of the nozzles of US 2007116650 (WO 05061090) is seven. These seven nozzles should then be placed with one nozzle at the central axis of the chamber and the other six nozzles symmetrically around this axis. This is analogous to preferred positioning for a chamber having three nozzles. See FIG. 4.

The arrangements illustrated in FIGS. 5a-b contain two or more collecting chambers (505a,b...) with at least one, two or more nozzles per collecting chamber. The nozzle external transport conduits for the fluid (516a,b, ...), for the solution (521a,b...) and for the make-up agent (539a,b...) are in the upstream direction connected to a storage tank for fluid, solution and/or make-up agent, respectively (not shown). The storage tank for the same kind of liquid, fluid and agent may be common for the nozzles/collecting chambers. On the downstream side of each chamber there is an outlet conduit (525a,b...) with a back-pressure regulator (526a,b...). The outlet conduits (525a,b ...) may merge before or after the back-pressure regulator to a common conduit (542) transporting the solvent/fluid mixture to waste or to a separating function in which the fluid is separated from the solvent and recycled back into the fluid stream of the arrangement.

The transport of fluid or solution to several spray nozzles from a common storage tank may be via a separate conduit for each nozzle without branching or via a starting common conduit that divides at one or more positions into one, two or more branch conduits (primary branch conduits) each of which is connected to one or more spray nozzles. If a primary branch conduit is connected to two or more spray nozzles, the primary branch conduit is further branched into secondary branch conduits etc. It can be appropriate to include an appropriate flow and/or pressure control function for equal transport of solution and fluid into each branch conduit leading to a spray nozzle in order to facilitate acceptable low inter-nozzle variability with respect to particle sizes and morphology complying with achieving preset (=predetermined) values for mean size, size distribution and morphology. This kind of function should regulate and control the back pressure regulator(s) downstream of the collecting chambers and/or pumps and/or valves upstream of the nozzle and/or the force pressing the upstream and downstream parts (231,331,232, 332) together.

As seen from FIGS. 4-5 a particle collecting chamber has preferably a circular cross-section, at least at the level of the spray nozzles.

The number of particle collecting chambers in an arrangement is typically one, but may also be two, three, four, five or more with typical upper limits 10 or 20.

At the downstream end of a chamber (105), there is typically an outlet for selective exit of the solution-fluid mixture depleted with respect to particle-forming substance, i.e. devoid of the particles produced in the chamber. In order to achieve this, a function (115) for separating the mixture from the particles formed, such as a filter, is typically included at the downstream end of the particle collecting chamber (105). This outlet is typically placed at a level below the spray outlet(s) of the nozzles.

In the case the production arrangement comprises two or more chambers and/or two or more nozzles as discussed above these chambers and/or nozzles can be run in sequence in order to produce a large batch of particles having predetermined size and morphological characteristics. In other words the particles produced in one chamber may be harvested while another chamber is started. See for instance U.S. Pat. No. 5,851,453 (WO 9501221), U.S. Pat. No. 6,063,188 and US 2006073087 (WO 9600610). Alternatively or in order to further increase the productivity in relation to a particular batch, several nozzles and/or chambers that are present in the same production arrangement can be run simultaneously. The term "simultaneously" in the context of a production arrangement comprising two or more chambers/nozzles includes that the time periods during which a chamber/nozzle is utilized at least partially overlaps with the time periods that is utilized by one, two or more of the other chambers/nozzles of the arrangement. The overlap may be anything from 100% down to above 0%, such as ≥1% or ≥5% or ≥10% or ≥25% or ≥50% etc. The exact overlap depends on practical considerations but the highest productivity for a production arrangement should be achievable for 100% overlap. Chambers and nozzles used in both the sequential and the simultaneous mode should be essentially equal.

Make-Up Agent

A make-up agent is an agent that when present in the fluid influences mean size, size distribution and/or morphology of the particles. The fluid may be in a subcritical state at the mixing as given for the innovative method but for other kinds of the method defined on page 1, $1^{st}$ paragraph the fluid may be in a supercritical state.

One kind of typical make-up agent is promoting nucleation and/or particle formation of the particle-forming substance in the solution and/or in the solution-fluid mixture, e.g. is an anti-solvent for the particle-forming substance. This kind of agent is typically also acting as precipitating agent.

Another kind of typical make-up agent is promoting solubilization of the particle-forming substance, e.g. is a solvent for the particle-forming substance.

Typical make-up agents may be selected amongst liquids that are capable of affecting the particle-forming substance as given in the preceding paragraphs. They preferably should be partly miscible with or dissolvable in the fluid and/or the solvent of the solution. In other words preferred make-up agents do not cause phase separations other than formation of the desired particles. Candidates are given under the heading "The solution stream and the fluid stream". Liquids forming azeotropes with one or more components of the solvent of the solution, may dehydrate or hydrate the particles formed etc and are therefore of particular interest.

The make-up agent can in principle be introduced into the arrangement at any position in the fluid stream, i.e. at any position upstream of the mixing arrangement (114). The introduction may thus be via a separate inlet conduit (217) connected to A) the internal transport conduit (210) for fluid (within the nozzle (201)), and/or B) the external transport conduit (116,216) guiding fluid to the nozzle (101,201), for instance in a heating function (141), and/or C) the arrangement at a position upstream of the external transport conduit (116), for instance to a storage tank (122) for fluid directly or indirectly attached to the upstream end of the external transport conduit (116) for the fluid, to a heating position (141) placed along the external transport conduit (116).

A make-up agent may be added alone to the system or in combination with one or more other components. These other components may encompass other make-up agents, a vehicle which preferably is miscible with the fluid and/or is a solvent for the make-up agent concerned etc. This includes that the fluid also may be used as a vehicle for the make-up agent. The composition used for introduction of a make-up agent may or may not be in the same state as the fluid, i.e. a sub- or a supercritical state. The conduit (139,239) through which a make-up agent is added to the fluid stream (103) is equipped with the appropriate valve function, pumps and other functions (140,240) for controlling flow velocity relative to the fluid flow (103).

The preferred position at which the make-up agent is added is within the external transport conduit (116,216) transferring fluid to the nozzle.

The addition of a make-up agent may be at one, two or more positions in the fluid stream. Different agents or the same agent may be introduced at different positions.

One way of adding a make-up agent can be accomplished if the fluid subsequent to step (iii) is separated from the solvent/solution and recycled to one of the positions at which the make-up agent is introduced into the system/arrangement. In many cases the fluid recycled in this way will contain residual amounts of the solvent in which the substance initially was dissolved or dispersed. These residual amounts will typically influence particle size and/or morphology of the particles formed thereby acting as a make-up agent. It is also possibly to add a separate make-up agent to the fluid recycled during its transport back into the main fluid stream, i.e. to add this kind of agent to the recycling conduit (119).

The proportion of make-up agent incorporated into the fluid stream is discussed elsewhere in this specification.

The Fluid Stream and the Solution Stream

The solvent and the fluid are miscible with each other. The particle-forming substance is soluble in the solvent but not in the fluid. By the expressions "soluble" and "but not" in this context are meant "more soluble" in the solvent than" in the fluid. See below.

Illustrative fluids that are used in a subcritical state in the method aspect of the invention of the invention are aqueous liquids at room temperature and atmospheric pressures. With preference they are also volatile at room temperature and atmospheric pressure. The water content in useful fluids are typically ≥50%, such as ≥60%, with preferences for ≥75%, such as ≥90% or ≥99% (v/v-%). In addition to water these fluids may also contain other liquid components and/or other agents that will render the fluid capable of acting as an atomizing agent and an anti-solvent. Liquid components other than water may be selected amongst the different solvents discussed for the solution. Such liquid components are typically water-miscible. See below. Other agents include pH-increasing or pH-decreasing agents, such as acids, bases and/or pH-buffering components that enables fluids which when mixed with the solution causes nucleation and particle formation in the mixture, e.g. precipitation.

Illustrative fluids that can be used as a supercritical fluid in the arrangement aspect of the invention are typically gaseous at room temperature and atmospheric pressures. As for the fluids of the preceding paragraph they are typically selected as being capable of acting as atomizing agents and anti-solvents against the particle-forming substance. Particular compounds/elements from which they can be selected are carbon dioxide (Pc=74 bar and Tc=31° C.), nitrous oxide (Pc=72 bar and Tc=36° C.), sulphur hexafluoride (Pc=37 bar and Tc=45° C.), ethane (Pc=48 bar and Tc=32° C.), ethylene (Pc=51 bar and Tc=10° C.), xenon (Pc=58 bar and Tc=16° C.), trifluoromethane (Pc=47 bar and Tc=26° C.), and chlorotrifluoromethane (Pc=39 bar and Tc=29° C.) and mixtures. Pc stands for critical pressure and Tc for critical temperature.

Illustrative liquids that are used as solvents in the solution together with either the supercritical or a subcritical fluid are typically in the liquid state but volatile at room temperature and atmospheric pressure. They are typically also capable of maintaining the particle-forming substance in dissolved form in the solution at the process temperature of the solution stream, i.e. the concentration of the dissolved substance shall be below the saturation concentration of the substance, typically ≤80% of the saturation concentration at the pressures and temperature applied upstream of the mixing arrangement. Suitable concentrations of the particle-forming substance in the solutions are typically found in the interval ≤20%, such as ≤10% or ≤5% or ≤3% with lower limits being ≤0.05% or 0.1% (all in w/v-%). The term "volatile" for solvents in the context of the invention typically means boiling points of ≤150° C., such as ≤110° C. or ≤100° C., at atmospheric pressure. Examples are inorganic solvents, including water as well as non-aqueous inorganic solvents, and organic solvents including symmetrical and unsymmetrical $C_{1-5}$ dialkyl ketones, such as acetone, butanone, pentanones etc, symmetrical and unsymmetrical $C_{1-5}$ dialkyl ethers, such as diethyl ether, methyl propyl ether, methyl butyl ether, methyl pentyl ether, ethyl propyl ether etc, $C_{1-5}$ alkanols including fluorinated forms and various primary, secondary, tertiary forms thereof, such as methanol, ethanol, iso propanol, n-propanol, various butanols and pentanols etc, $C_{1-5}$ alkyl esters of $C_{1-5}$ carboxylic acids, such as ethyl actetate, dimethylsulphoxide, N,N-dimethyl formamide, acrylonitrile etc. A potential useful fluorinated alkanol is trifluoroethanol. The term solvent includes mixtures of miscible liquids. The solutions may contain agents that enhances or diminishes the solubility of the particle-forming substance, e.g. pH-increasing, pH-decreasing and/or buffer components. This in particular may apply if the solvent is aqueous and used together with an aqueous fluid in the method aspect of the instant invention.

In the method aspect of the invention the water content of the solvent of the solution may vary within wide limits with the proviso that high water contents (e.g. >25 v/v-%) typically means that the solution has to contain a solubility enhancing agent and/or the fluid has to contain a solubility decreasing agent, preferably a precipitating agent. Thus the water content of the solvent typically is ≤50%, such as ≤40% with preferences for ≤25%, such as ≤10% or ≤1% (v/v-%). Solubility in this context refers to the solubility of the particle-forming substance.

Particle-Forming Substance

The term "substance" shall in the context of the invention be interpreted broadly including single compounds as well as mixtures of compounds even if the typical substance to be transformed represents a single compound or a mixture of compounds having similar chemical and physical characteristics. Many of the substances to be transformed to particles in the method are biologically active or works as a vehicle, an additive, an excipient etc in the compositions into which the particles are to be incorporated after their production according to the invention. The most important substances are to be used pharmacologically meaning that the term "biologically active" mostly also stands for "therapeutically active". The substances may be water-soluble or water-insoluble at the desired concentration in the solution to be used in the invention. They may exhibit polypeptide structure and/or non-polypeptide structure, such as nucleotide structure, carbohydrate structure, lipid structure, steroid structure, be a hormone, a sedative, an anti-inflammatory substance etc.

The particle-forming substance is soluble in the solvent but not in the fluid, and thus typically has a higher solubility in the solvent than in the fluid, e.g. with a factor ≥5, such as ≥10 or ≥25 or ≥50 or ≥100. An increase in the factor will typically lead to advantages in the method aspect of the invention.

A pharmaceutical formulation of the invention comprises a therapeutically active component (drug) that has been incorporated into the formulation together with optional pharmaceutically acceptable carriers/vehicles, additives etc. At least one of the components of the formulation, typically a therapeutically active ingredient, such as the drug, or a vehicle or an additive has been used in the form of particles manufactured according to the method presented herein. Typical formulations are tablets, capsules, pills, pellets, dispersions, sprays, ointments, solutions etc.

EXPERIMENTAL PART

Example 1

A 2% w/v budesonide solution in acetone was introduced into the nozzle of FIG. 2 placed in the arrangement of FIG. 1 (except for the recycling capability) using a separate high-performance liquid chromatography pump 1.4 ml/min, together with the 125 g/min $scCO_2$ (about 150 ml/min) which was modified with the make-up agent 4.2 ml/min acetone. The pressure in the system was 100 atm. and temperature was at 60° C. All of the streams contact within the nozzle and the budesonide powder formed and collected in the particle collecting chamber. The $scCO_2$ and acetone was drained via the backpressure regulator outlet. Then, a further washing process was performed to eliminate the solvent mixed in the $scCO_2$. After the washing process, the $CO_2$ was slowly drained off from the chamber. Once the $CO_2$ had been completely removed, the particles on the filter and on the wall were collected for analysis. The particles were characterized by laser diffraction in Mastersizer 2000 (Malvern Instruments Ltd, Worcestershire, United Kingdom).

Example 2

A further experiment was performed with the apparatus used in example 1. The process parameters were set to the same values as in example 1 except for the flow velocity of the make-up agent that now was 2.1 ml/min.

Example 3

A further experiment was performed with the apparatus used in Example 1, for control of reproducibility. The process parameters were set to the same values as in Example 1.

Example 4

A further experiment was performed with the apparatus used in Example 1. The process parameters were set to the same values as in Example 1, except for the flow velocity of the make-up agent that now was 1.4 ml/h.

Example 5

A further experiment was performed with the apparatus used in Example 1. The nozzle used was exchanged with a newly manufactured nozzle of the same kind. The process parameters were set to the same values as in Example 1.

Results Examples 1-5

|  | Particle size distribution | | | Spec. |
|---|---|---|---|---|
| Example | D(0.1') | d(0.5)' | d(0.9)' | Surface Area $m^2/g$ |
| 1 | ≤1.9 μm | ≤4.0 μm | ≤7.9 μm | 1.7 |
| 2 | ≤1.1 μm | ≤1.9 μm | ≤3.4 μm | 1.7 |
| 3 | ≤2.2 μm | ≤4.2 μm | ≤8.7 μm | 1.6 |
| 4 | ≤6.3 μm | ≤14.2 μm | ≤26.7 μm | 0.6 |
| 5 | ≤2.0 μm | ≤4.1 μm | ≤7.9 μm | 1.7 |

*Columns d(0.1), d(0.5) and d(0.9) give the diameter for the smallest particles up to 10%, 50% and 90% of the material analyzed. The value for column d(0.5) will in this specification be called mean particle size of the batch studied.

Example 6

Solvent=Acetone and Fluid=Water

The production arrangement used is shown in FIG. 6. It had two high pressure pumps (Jasco PU 980). One of the pump (624*b*) is used to feed the solution (0.2 ml/min Piroxicam in acetone (2% w/v)) (602) via a transport conduit (621) and the other pump (624*a*) is used to feed 10 ml/min water (fluid, anti-solvent) (603) via transport conduit (616) to a spray nozzle (601) placed in a particle collection chamber (605) containing at its outlet (625) a function for separating particles (filter) (615). The nozzle internal transport conduits were two stainless steel tubes (610,612) that were placed coaxially to each other with the inner one (612) connected to the pump (624b) for the solution and the outer one (610) to the pump (624a) for fluid. After particles had been formed, the chamber (605) was purged with $N_2$ to remove water and acetone. Particle morphology and size were examined using TM-1000 Hitachi scanning electron microscope. Particle sizes were determined to be less than 3 μm. A few agglomerates could be observed.

Example 7

The production arrangement used is shown in FIG. 7. A high pressure pump (Thar P50) (724a) is used to feed 50 ml/min water (fluid, anti-solvent) (703) via a transport conduit (716) and a high pressure pump (Jasco PU 980) (724b) is used to feed 1 ml/min solution of Piroxicam in acetone (2% w/v) (702) via transport conduit (721) to a nozzle (701) placed in a particle collecting chamber (705) containing at its outlet (725) a particle separation function in the form of a filter cup (715). The nozzle was of the same kind as given in FIG. 2. The transport conduit (716) for the fluid stream (703) was connected to the outer conduit and the transport conduit (721) for the solution stream (702) to the inner conduit. After particle formation the chamber (705) was purged with $N_2$ to remove water and acetone. The morphology and size of the crystals in the filter cup is determined using TM1000 Hitachi scanning electron microscope. Particle sizes were determined to be between 0.5 μm to 2 μm. A few agglomerates were observed.

While the invention has been described and pointed out with reference to operative embodiments thereof, it will be understood by those skilled in the art that various changes, modifications, substitutions and omissions can be made without departing from the spirit of the invention. It is intended therefore that the invention embraces those equivalents within the scope of the claims which follow.

The invention claimed is:

1. A method for controlling size and/or morphology characteristics of particles when producing a batch of particles of a substance in a production arrangement, said particles having predetermined sizes and/or morphology, comprising the steps of:
   i) mixing within a spray nozzle and under flow conditions a stream of a liquid solution in which the substance is dissolved or dispersed with a stream of a fluid, the kind of solvent in the solution, the kind of fluid and the proportion of the volume of the solution relative to the volume of the fluid being selected to promote nucleation and particle formation of the substance in the mixture,
   ii) passing said mixture in the form of a spray through a spray outlet of the nozzle into a particle collecting chamber, and
   iii) separating and collecting within said chamber said particles from said mixture, wherein
   the solvent is a liquid and the fluid is an aqueous liquid in a subcritical state,
   the pressure upstream and downstream of the spray nozzle is >1 bar and ≤30 bar, and
   the pressure drop across the spray nozzle is ≤30 bar.

2. The method of claim 1, wherein said fluid and said solvent are miscible with each other causing no phase separation into liquid/fluid phases upon mixing.

3. The method of claim 1, wherein the concentration of the particle-forming substance in the solution is below the saturation concentration of the substance at the pressures and temperature applied at mixing.

4. The method of claim 1, wherein steps (i) and (ii) are performed simultaneously in two or more separate and essentially identical spray nozzles of the same production arrangement containing at least one particle collecting chamber, with at least two of the nozzles being in spray communication with the same particle collecting chamber.

5. The method of claim 1, wherein the predetermined mean diameter of the particles of the batch is selected to be ≤20 μm.

6. The method of claim 1, wherein the mixing is initiated by merging the fluid stream and the solution stream at an angle selected in the interval of 30°-150°.

7. The method of claim 1, wherein
   A) said nozzle comprises
      a) two internal transport conduits for the solution and the fluid, respectively, which conduits are coaxial at least in their upstream parts, and in their downstream ends are merging with each other into
      b) a mixing arrangement followed by and/or coinciding with
      c) a spray outlet, where
      a1) the downstream part of one of the two internal transport conduits is cylindrical providing for cylindrical flow at the position of merging with the other conduit, and the downstream part of the other one of the conduits is disc-shaped providing an annular flow that is directed radially outwards from a centre which coincides with the axis of the cylindrical flow, the merging angle between the two conduits being selected in the interval of 30°-150°,
      b1) the mixing arrangement is annular comprising an annular upstream end at the merging of the two internal transport conduits and an annular downstream end, and
      c1) the spray outlet is annular and communicates in the upstream direction with the annular downstream end of the mixing arrangement, and
   B) performing step (i) in said mixing arrangement and step (ii) in said spray outlet.

8. The method of claim 7, wherein the inner one of the two coaxial internal transport conduits is cylindrical in its downstream end and the outer one is disc-shaped in its downstream end.

9. The method of claim 7, wherein the two internal coaxial transport conduits are coaxial to their point of merging.

10. The method of claim 7, comprising passing the solution stream through the inner one of the internal transport conduits that are coaxial in their upstream end and the fluid stream through the outer one of these conduits.

11. The method of claim 1, wherein the particles obtained in step (iii) are incorporated as an ingredient into a pharmaceutical formulation containing a therapeutically active substance possibly combined with other ingredients.

12. The method of claim 1, wherein the fluid has a water content of ≥50% (v/v).

13. The method of claim 12, wherein the fluid has a water content of ≥90% (v/v).

14. The method of claim 3, wherein the concentration of the particle-forming substance in the solution is ≥1% and ≤80% of the saturation concentration at the pressures and temperature applied at mixing.

15. The method of claim 1, wherein steps (i) and (ii) are performed simultaneously in two or more separate and essentially identical spray nozzles of the same production arrangement containing at least one particle collecting chamber, with every one of the particle collecting chambers containing at least one nozzle.

16. The method of claim 5, wherein the predetermined mean diameter of the particles of the batch is selected to be ≤10 μm.

17. The method of claim 1, wherein the size distribution of the particles in the batch is that 80% of the particles have sizes of ≤20 μm.

18. The method of claim 6, wherein the mixing is initiated by merging the fluid stream and the solution stream at an angle of 90°.

19. The method of claim 1, wherein the mixing is initiated by merging the fluid stream and the solution stream at an angle of 0°.

20. The method of claim 1, wherein the pressure drop across the spray nozzle is ≥1.25